United States Patent
Kasai et al.

(10) Patent No.: US 8,233,049 B2
(45) Date of Patent: Jul. 31, 2012

(54) IMAGING USING AN ELECTROMAGNETIC WAVE

(75) Inventors: Shintaro Kasai, Tokyo (JP); Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 105 days.

(21) Appl. No.: 12/300,791

(22) PCT Filed: Aug. 27, 2008

(86) PCT No.: PCT/JP2008/065795
§ 371 (c)(1),
(2), (4) Date: Nov. 13, 2008

(87) PCT Pub. No.: WO2009/028718
PCT Pub. Date: Mar. 5, 2009

(65) Prior Publication Data
US 2010/0171835 A1    Jul. 8, 2010

(30) Foreign Application Priority Data

Aug. 31, 2007  (JP) .................................. 2007-226339
Jun. 19, 2008  (JP) .................................. 2008-160767

(51) Int. Cl.
    *H04N 5/30* (2006.01)
(52) U.S. Cl. ....................................... 348/162; 348/164
(58) Field of Classification Search .................. 348/162, 348/164
See application file for complete search history.

(56) References Cited

U.S. PATENT DOCUMENTS

| 5,623,145 | A | 4/1997 | Nuss |
| 7,248,995 | B2 | 7/2007 | Itsuji et al. ..................... 702/159 |
| 7,548,508 | B2 * | 6/2009 | Geile et al. ..................... 370/208 |
| 7,683,778 | B2 * | 3/2010 | Ouchi ......................... 340/539.1 |
| 7,692,147 | B2 * | 4/2010 | Hu et al. ..................... 250/336.1 |
| 2004/0263379 | A1 | 12/2004 | Keller |
| 2005/0110672 | A1 | 5/2005 | Cardiasmenos et al. |
| 2006/0197021 | A1 | 9/2006 | Ouchi ........................... 250/343 |
| 2006/0219922 | A1 | 10/2006 | Watanabe et al. |
| 2007/0030115 | A1 | 2/2007 | Itsuji et al. ..................... 340/5.8 |
| 2007/0195921 | A1 | 8/2007 | Ouchi ............................. 378/1 |
| 2007/0229094 | A1 | 10/2007 | Kasai et al. ..................... 324/639 |
| 2007/0235718 | A1 | 10/2007 | Kasai et al. ..................... 257/21 |
| 2008/0040763 | A1 * | 2/2008 | Geile et al. ..................... 725/118 |
| 2008/0314152 | A1 | 12/2008 | Ouchi ............................. 73/597 |
| 2009/0238065 | A1 * | 9/2009 | Dapper et al. ................ 370/208 |

FOREIGN PATENT DOCUMENTS

JP   8-320254   12/1996

(Continued)

OTHER PUBLICATIONS

U.S. Appl. No. 12/196,224, filed on Aug. 21, 2008, Inventors; Kousuke Kajiki, Toshthiko Ouchi, and Ryota Sekiguchi.

(Continued)

*Primary Examiner* — Mohamed Wasel
(74) *Attorney, Agent, or Firm* — Fitzpatrick, Cella, Harper & Scinto

(57) ABSTRACT

An object of examination is irradiated with an electromagnetic wave including a frequency component from 30 GHz to 30 THz and a Fourier transform image of the transmitted or reflected electromagnetic wave from the object of examination is obtained. The obtained Fourier transform image is subjected to a spatial frequency filtering processing. This method can visualize only the part to be visualized in an imaging operation using a terahertz wave.

16 Claims, 13 Drawing Sheets

FOREIGN PATENT DOCUMENTS

| | | |
|---|---|---|
| JP | 2004-286716 | 10/2004 |
| WO | 03/042670 | 5/2003 |
| WO | 2006/078570 | 7/2006 |
| WO | 2006/119609 | 11/2006 |

OTHER PUBLICATIONS

Communication Pursuant to Article 94(3) EPC dated Feb. 24, 2011 in corresponding European Application No. 08828284.3.

PCT International Search Report and Written Opinion of the International Searching Authority in International Application No. PCT/JP2008/065795, Mailing Date Jan. 29, 2009.

International Preliminary Report on Patentability dated Mar. 11, 2010 in corresponding International Application PCT/JP2008/065795.

* cited by examiner

FIG. 3
(a) BINARIZED REAL IMAGE
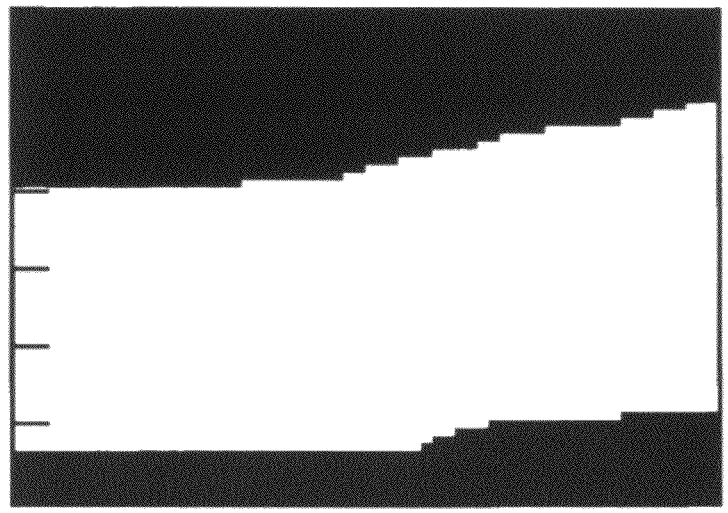
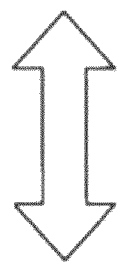
(b) FOURIER TRANSFORM IMAGE
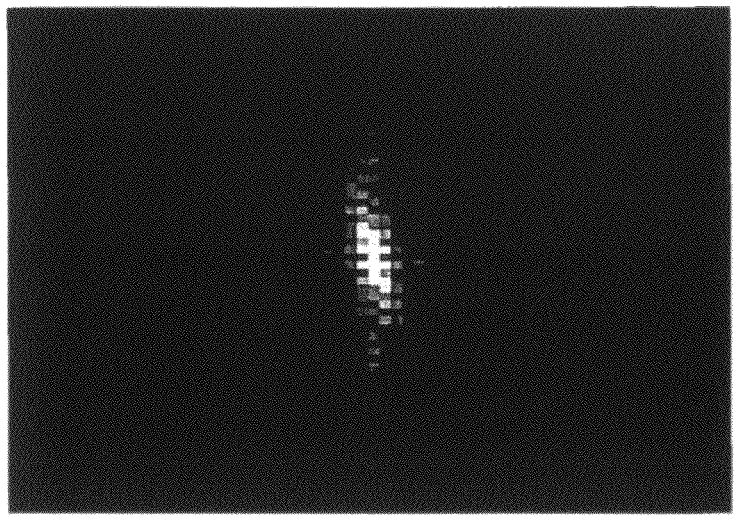

FIG. 4
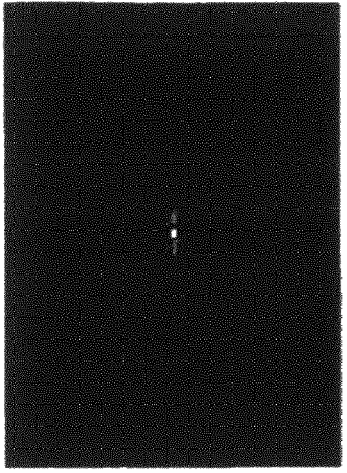
(c) INVERSE FOURIER TRANSFORM IMAGE
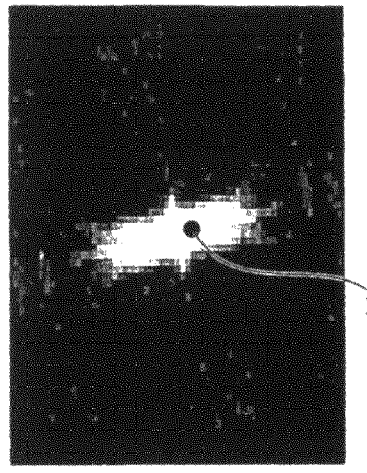
(d) INVERSE FOURIER TRANSFORM IMAGE
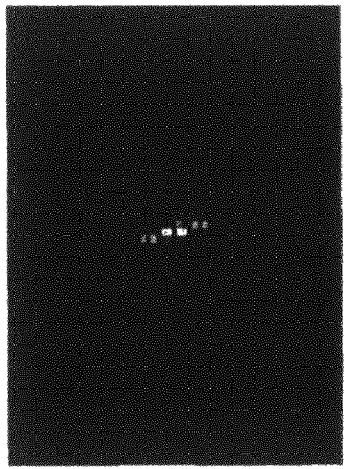
(a) FOURIER TRANSFORM IMAGE AFTER FILTERING PROCESSING
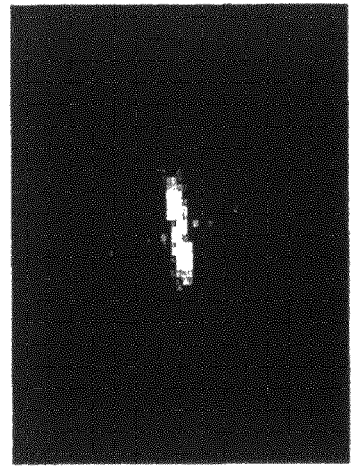
(b) FOURIER TRANSFORM IMAGE AFTER FILTERING PROCESSING

IMAGING USING AN ELECTROMAGNETIC WAVE

TECHNICAL FIELD

This invention relates to an imaging method and an imaging apparatus employing an electromagnetic wave in the frequency range of not less than 30 GHz and not more than 30 THz including so-called millimeter waves and terahertz waves (to be referred to inclusively as "terahertz wave" hereinafter).

BACKGROUND ART

The technological development utilizing the terahertz wave has been vigorously in progress in recent years. Technologies that utilize the terahertz wave and exploit the physical property thereof that the terahertz wave can be transmitted through various substances are expected to find promising applications particularly in the field of imaging.

Japanese Patent Registration No. 03387721 discloses a technique relating to a method of visualizing the inside of an object such as hand-carry baggage or some other personal belonging, using the terahertz wave. According to the above-cited patent document, a transparent image of an object can be obtained by irradiating a pulse-shaped terahertz wave onto a point of the object, detecting the terahertz wave transmitted through the object and shifting the object.

Methods of examining a sealed letter have also been proposed besides the techniques of examining hand-carry baggage. Japanese Patent Application Laid-Open No. 2004-286716 discloses a method of detecting a prohibited drug such as a narcotic hidden in a sealed letter. This method utilizes the absorption spectrum that the prohibited drug such as a narcotic characteristically shows relative to the terahertz wave to identify the prohibited drug in the inside without opening the sealed letter.

DISCLOSURE OF THE INVENTION

However, when such a method of seeing through the inside of an object by means of the terahertz wave is applied to a person, the method can constitute an invasion of privacy relative to the person because the terahertz wave transmitted through the clothes and reflected and scattered by the skin surface of the person is detected to form an image.

Blank paper and paper where characters are written by means of a pencil or a pen and ink show different transmittances relative to the terahertz wave. Therefore, when a method of detecting a narcotic without opening a sealed letter by means of the terahertz wave is employed, some or all of the characters on the letter may be read. This also can constitute an invasion of privacy and additionally can lead to censorship.

Thus, imaging using the terahertz wave is accompanied by a problem that the imaging can visualize a part that needs to be visualized and also a part that should not be visualized.

The present invention provides an imaging method and an imaging apparatus that can visualize only a part that needs to be visualized but does not visualize any part that should not be visualized.

In an aspect of the present invention, there is provided an imaging method including: a step of irradiating an object of examination with an electromagnetic wave including at least a frequency component from 30 GHz to 30 THz; a step of obtaining a Fourier transform image of the transmitted electromagnetic wave or the reflected electromagnetic wave from the object of examination by an optical unit; and a step of executing a spatial frequency filtering processing on the Fourier transform image.

In another aspect of the present invention, there is provided an imaging apparatus including: a mechanism for irradiating an object of examination with a collimated and coherent electromagnetic wave including a frequency component from 30 GHz to 30 THz; a mechanism for acquiring a Fourier transform image of the transmitted electromagnetic wave or the reflected electromagnetic wave from the object of examination by an optical unit; and a mechanism for executing a spatial frequency filtering processing on the Fourier transform image.

In still another aspect of the present invention, there is provided an imaging apparatus including: a mechanism for irradiating an object of examination with a coherent electromagnetic wave including a frequency component from 30 GHz to 30 THz; a mechanism for acquiring a Fourier transform image of the transmitted electromagnetic wave or the reflected electromagnetic wave from the object of examination by an optical unit; a mechanism for executing a spatial frequency filtering processing on the Fourier transform image; and a mechanism for executing an inverse Fourier transform on the Fourier transform image subjected to the spatial frequency filtering processing.

In still another aspect of the present invention, there is provided an imaging method using a terahertz wave including: a generation step of generating a terahertz wave; a step of acquiring a first Fourier transform image of an object of examination, using the terahertz wave generated in the generation step and transmitted through or reflected by the object of examination; a step of acquiring a second Fourier transform image to be used as spatial frequency filter for the first Fourier transform image; and a step of executing an arithmetic operation processing on the first Fourier transform image and the second Fourier transform image.

Thus, according to the present invention, only a part that needs to be visualized can be visualized and any part that should not be visualized is not visualized in an imaging operation so that privacy and confidentiality of communication can be protected in an examination of hand carry baggage or some other personal belonging or a sealed letter.

Further features of the present invention will become apparent from the following description of exemplary embodiments with reference to the attached drawings.

BRIEF DESCRIPTION OF THE DRAWINGS

FIG. 3 is a schematic illustration of the image employed as spatial frequency filter in Example 1.

FIG. 4 is a schematic illustration of the image obtained after the filtering processing in Example 1.

BEST MODE FOR CARRYING OUT THE INVENTION

Figure 1:
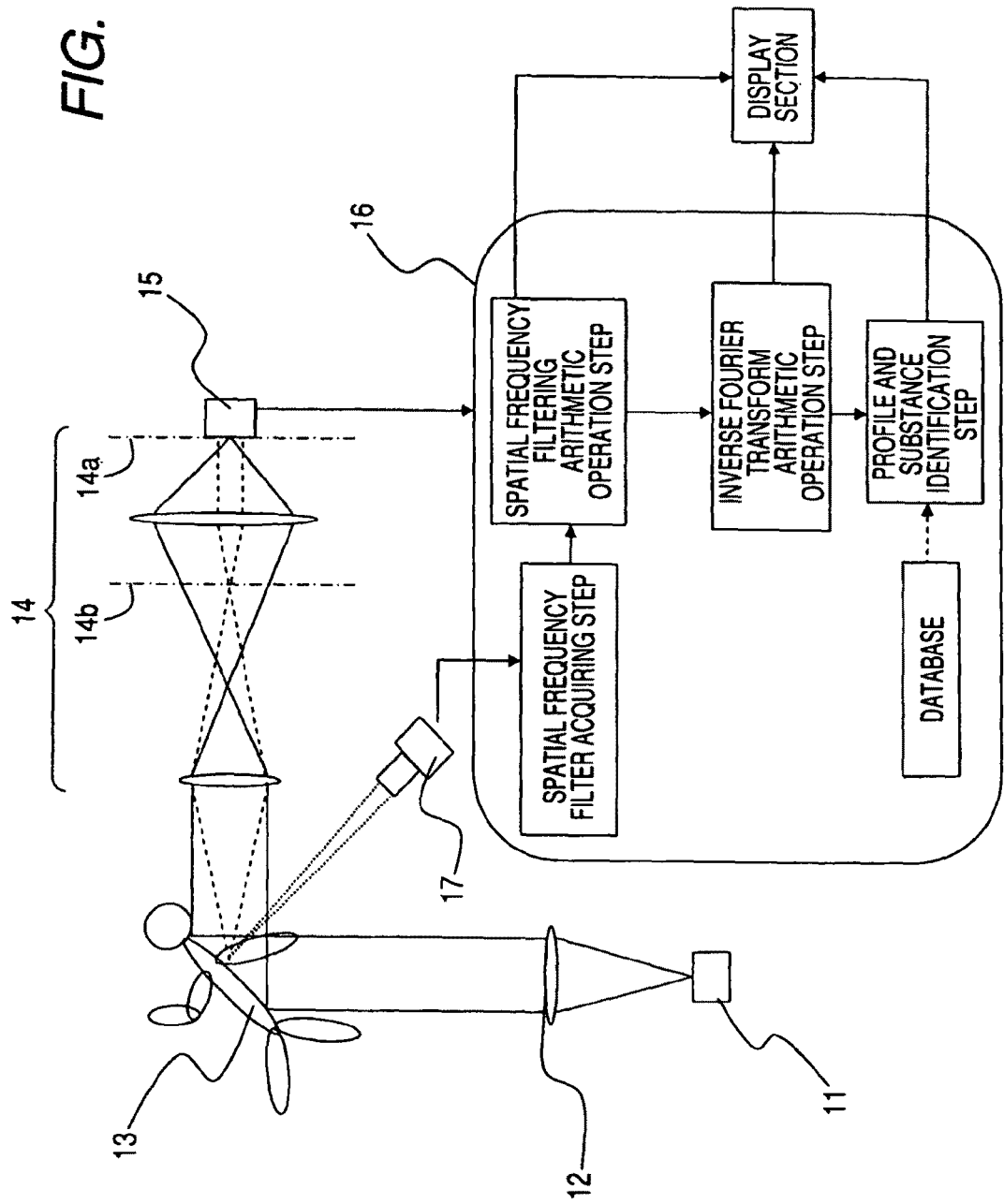
FIG. 1 is a schematic illustration of the imaging method and the image apparatus of Example 1.

An imaging method using a terahertz wave according to the present invention has the following steps:

(a) a generation step of generating a terahertz wave;

(b) a step of acquiring a first Fourier transform image of an object of examination, using the terahertz wave generated in the generation step and transmitted through or reflected by the object of examination;

(c) a step of acquiring a second Fourier transform image to be used as spatial frequency filter for the first Fourier transform image; and (d) a step of executing an arithmetic operation processing on the first Fourier transform image and the second Fourier transform image.

In this specification, an electromagnetic wave including at least a frequency component not less than 30 GHz and not more than 30 THz is referred to as the terahertz wave. The terahertz wave has a property of being transmitted through substances, particularly showing a high transmittance to substances that are formed by non-polar molecules. Additionally, the frequency band of terahertz wave is a frequency band where spectrums specific to substances appear.

Now, the steps (a) through (d) will be described in detail below.

(a) Generation Step of Generating a Terahertz Wave

Devices that can generate a terahertz wave include Gunn diodes and quantum cascade lasers.

Alternatively, a terahertz wave can be generated by irradiating a laser beam on a photoconductive device. When the laser beam being irradiated is pulse-shaped, a pulse wave that includes the frequency band of terahertz wave is generated. On the other hand, when light formed by combining two laser beams having different frequencies is irradiated onto a photoconductive device, a continuous wave including the frequency band of terahertz wave is generated. Such combined light becomes a wave having a frequency that corresponds to the difference of the frequencies of the two laser beams. A frequency shifter may appropriately be used to make two laser beams have different frequencies.

The techniques that can be used to generate a terahertz wave for the purpose of the present invention are not limited to those described above. This step will be described later in greater detail by way of the examples.

(b) Step of Acquiring a First Fourier Transform Image

A step of collimating the generated terahertz wave is preferably included after the generation step of generating a terahertz wave. Then, as a result, a first Fourier transform image can be optically accurately acquired. A lens made of a resin such as Teflon (trademark) or polyethylene may be used to collimate the generated terahertz wave to produce a parallel beam of light, although the present invention is by no means limited thereto. This step will be described later in greater detail by way of Example 1.

This step of acquiring a first Fourier transform image preferably includes the following steps. The first step is a step of optically acquiring a real image of the object of examination by means of the terahertz wave generated in the generation step and transmitted through or reflected by the object of examination. The second step is a Fourier transform step of electrically executing an arithmetic operation processing on the real image. As a result, the first Fourier transform image can be electrically acquired as pointed out above. These steps will be described later in greater detail by way of Example 5.

(c) Step of Acquiring a Second Fourier Transform Image

The step of acquiring a second Fourier transform image preferably includes the following steps. The first step is a step of acquiring a real image of an object of examination by means of visible light. The second step is a step of acquiring a binarized image of the real image. Additionally, the third step is a Fourier transform step of electrically executing an arithmetic operation processing on the binarized image. As a result, the second Fourier transform image can be electrically acquired. These steps will be described later in greater detail by way of Example 1.

Alternatively, the step of acquiring a second Fourier transform image preferably includes the following steps. The first step is a step of generating a second terahertz wave having a center frequency different from the terahertz wave generated in the generation step to acquire a first Fourier transform image. The second step is a step of optically acquiring a Fourier transform image of the second terahertz wave transmitted through or reflected by the object of examination. As a result, a substance having a specific fingerprint spectrum relative to a certain frequency can be extracted with ease from a mixture of a plurality of substances. These steps will be described later in greater detail by way of Example 2.

Furthermore, the step of acquiring a second Fourier transform image preferably includes the following steps. The first step is a step of reading out a body profile that corresponds to the object of examination from average body profiles of different sexes, different ages and different nationalities stored in advance. Then, the second step is a step of Fourier transforming the body profile that corresponds to the object of examination. As a result, the second Fourier transform image can be acquired without newly acquiring an image from the object of examination.

(d) Step of Executing an Arithmetic Operation Processing

The first Fourier transform image and the second Fourier transform image are preferably subjected to an arithmetic operation processing. Particularly, subtraction is preferably conducted. A technique of normalization and/or that of weighting may be used for the subtraction. Alternatively, the arithmetic operation processing may be executed optically. These steps will be described later in greater detail by way of Example 3.

The second Fourier transform image is preferably subtracted from the first Fourier transform image by means of an electric arithmetic operation processing in this step processing.

(Inverse Fourier Transform Step)

The imaging method according to the present invention preferably further includes a step of acquiring an inverse Fourier transform image of the image acquired in the step of executing arithmetic operation processing on the first Fourier transform image and the second Fourier transform image.

Now, the imaging method employing a terahertz wave according to the present invention will be described in greater detail hereinafter by way of the examples.

EXAMPLE 1

A Visual Light Image is Binarized and Subjected to Fourier Transform and then Further to Spatial Frequency Filtering Now, the imaging method and the imaging apparatus of Example 1 will be described below by referring to the related drawings. FIG. 1 is a schematic illustration of the system of the imaging method of Example 1.

The terahertz wave emitted from a light source 11 that is designed to generate a coherent terahertz wave is collimated to parallel rays of light by means of a terahertz wave irradiation optical system 12 and irradiated onto an object of examination 13. The terahertz wave that is reflected/scattered/diffracted by the object of examination 13 (at least a terahertz wave out of the transmitted electromagnetic wave and the reflected electromagnetic wave) forms a Fourier transform image on a Fourier transform plane 14a by way of a Fourier transform optical system 14. The Fourier transform optical system 14 is formed by using one or more than one lenses or one or more than one mirrors in combination. While the specific structure of the Fourier transform optical system 14 is described hereinafter mainly in terms of one or more than one lenses, they may be replaced by mirrors that operate to the same effect. A detector 15 is arranged on the Fourier transform plane 14a to acquire a terahertz wave Fourier transform image of the object of examination 13.

The acquired Fourier transform image is a spatial Fourier transform image of the object of examination 13. Low frequency spatial frequency components are distributed near the center of the image, whereas high frequency spatial frequency components are distributed in the peripheral area of the image. The acquired Fourier transform image is then transmitted to a computer 16 as electronic information and subjected to electronic spatial frequency filtering in a spatial frequency filtering arithmetic operation processing step. The filtering processing may vary depending on the object of examination. The specific filtering processing method relative to an object of examination will be described later in greater detail.

The image information subjected to filtering processing is then sent to a display section and the image is displayed on a display so that the examiner can see the image. When the examiner can hardly comprehend the image of the image information subjected to filtering processing if the image information is displayed straight, the image information may further be subjected to an electronic inverse Fourier transform arithmetic operation processing and the image obtained by way of the processing may be displayed on the display section. Alternatively, the information subjected to a spatial frequency filtering processing or an inverse Fourier transform arithmetic operation processing may be checked by referring to a database to identify the profile and the substance of an object existing in the inside of the object of examination 13 in order to assist the examiner to detect a hazardous object.

An optimum arithmetic operation processing is selected according to the object of examination and the purpose of examination and executed in the spatial frequency filtering arithmetic operation step. Assume here that the object of examination 13 is a person who may bear a nonmetal edged tool typically made of ceramic for the following detailed description.

A Gunn diode that generates an electromagnetic wave of a frequency of about 0.1 THz is employed for terahertz light source 11. The terahertz wave emitted from the light source 11 is collimated to become a parallel beam with a diameter of about 30 cm by a terahertz irradiation optical system 12. A lens made of a resin such as Teflon (trademark) or polyethylene may be used for the terahertz wave irradiation optical system 12. Alternatively, a mirror may be used. Still alternatively, a phased array system formed by arranging a plurality of Gunn diodes in array that are adapted to generate terahertz waves in phase so as to directly generate a collimated coherent terahertz wave may be used.

The collimated terahertz wave is irradiated onto the object of examination 13. The collimated terahertz wave has a diameter of about 30 cm and hence cannot irradiate the entire body of the object of examination 13 at a time. In other words, the collimated terahertz wave is irradiated onto part of the object of examination 13. The terahertz wave is transmitted through the clothes of the object of examination 13 and reflected/scattered by the skin under the clothes. The terahertz wave that is reflected/scattered is then made to pass through a Fourier transform optical system 14 to form a spatial Fourier transform image of the inside of the clothes that the object of examination 13 wears on the Fourier transform plane 14a.

Detection devices each of which is formed by a Schottky diode and a reception antenna and that are arranged in array may typically be employed for the terahertz wave detector 15. As an example, an array antenna type detector with about 20 cm long sides formed by arranging 64×64 detection devices in array, each having dimensions 3×3 mm, may be employed. The Fourier transform optical system 14 necessary for acquiring a terahertz Fourier transform image with spatial frequencies down to 0.2 mm$^{-1}$ (spatial resolution of 5 mm) by means of the array antenna type detector will be discussed below.

If the spatial frequency is u (unit: mm$^{-1}$) and the focal length of the Fourier transform optical system is f (unit: mm), while the wavelength of the terahertz wave is λ (unit: mm) and the distance from the optical axis on the Fourier transform plane (which corresponds to the height of the image) is y (unit: mm), it is known that the relation shown below holds true.

$$u=y/(\lambda f)$$

If u=0.2 (and hence the spatial resolution is about 5 mm) and y=100 (the distance from the center to the periphery of the array antenna type detector), while λ=3, the focal length of which the Fourier transform optical system 14 is required of is 167 mm. If the Fourier transform optical system 14 is formed by a single lens, a Fourier transform image can be obtained by making an f-f arrangement of arranging the object of examination 13 and the detector 15 respectively at the frontside focus and at the backside focus. However, with such an arrangement, the object of examination can feel an oppressive sensation if the object is a person and the Fourier transform optical system can collide with the object of examination 13 if the object has a jaggy surface. Additionally, the Fourier transform optical system 14 can interfere with the terahertz wave irradiation optical system 12 depending on the configuration of the apparatus.

Therefore, an arrangement of taking a longer focal length, e.g., 50 cm (500 mm) for the lens will be discussed below in order to avoid the above-identified problems. When an array antenna detector 15 of the same size is employed, the spatial frequency is about 6.7×10$^{-3}$ mm$^{-3}$ and hence the spatial resolution is about 150 mm from the formula of u=y/(λf). The part that corresponds to the spatial frequency of 0.2 appears at a position separated from the optical axis by about 30 cm.

Therefore, sufficiently high spatial frequency components can be obtained by scanning the detector 15 over this region. A technique of acquiring a Fourier transform image in a shorter time will be described below.

The Fourier transform optical system 14 is made to have a structure formed by a lens group of a plurality of lenses in order to provide a sufficient length between the object of examination 13 and the Fourier transform optical system 14 and form a Fourier transform image that includes practically satisfactory spatial frequencies in the size of the detector 15. The optical system is so designed as to make the distance between the foremost surface (the optical surface closest to the object of examination 13) of the lens group and the object of examination 13 longer than the distance between the rearmost surface (the optical surface closest to the detector 15) of the lens group and the detector 15. The lenses may be replaced by mirrors. The distance between the foremost surface of the lens group (the optical surface closest to the object of examination 13) and the object of examination 13 is referred to as front focus, whereas the distance between the rearmost surface of the lens group (the optical surface closest to the detector 15) and the detector 15 is referred to as back focus.

For instance, a convex lens having a focal length of about 50 cm is arranged at a position separated from the object of examination 13 by 100 cm as the first lens. Then, another convex lens having a focal length of about 15 cm is arranged at a position separated from the first lens by 115 cm as the second lens. The terahertz detector 15 is arranged at a position separated from the second lens by 15 cm. The terahertz Fourier transform optical system 14 may be formed by the two lenses including the first lens and the second lens. If such is the case, the first lens operates as a relay lens for relaying an image of the object of examination 13.

Figure 2:
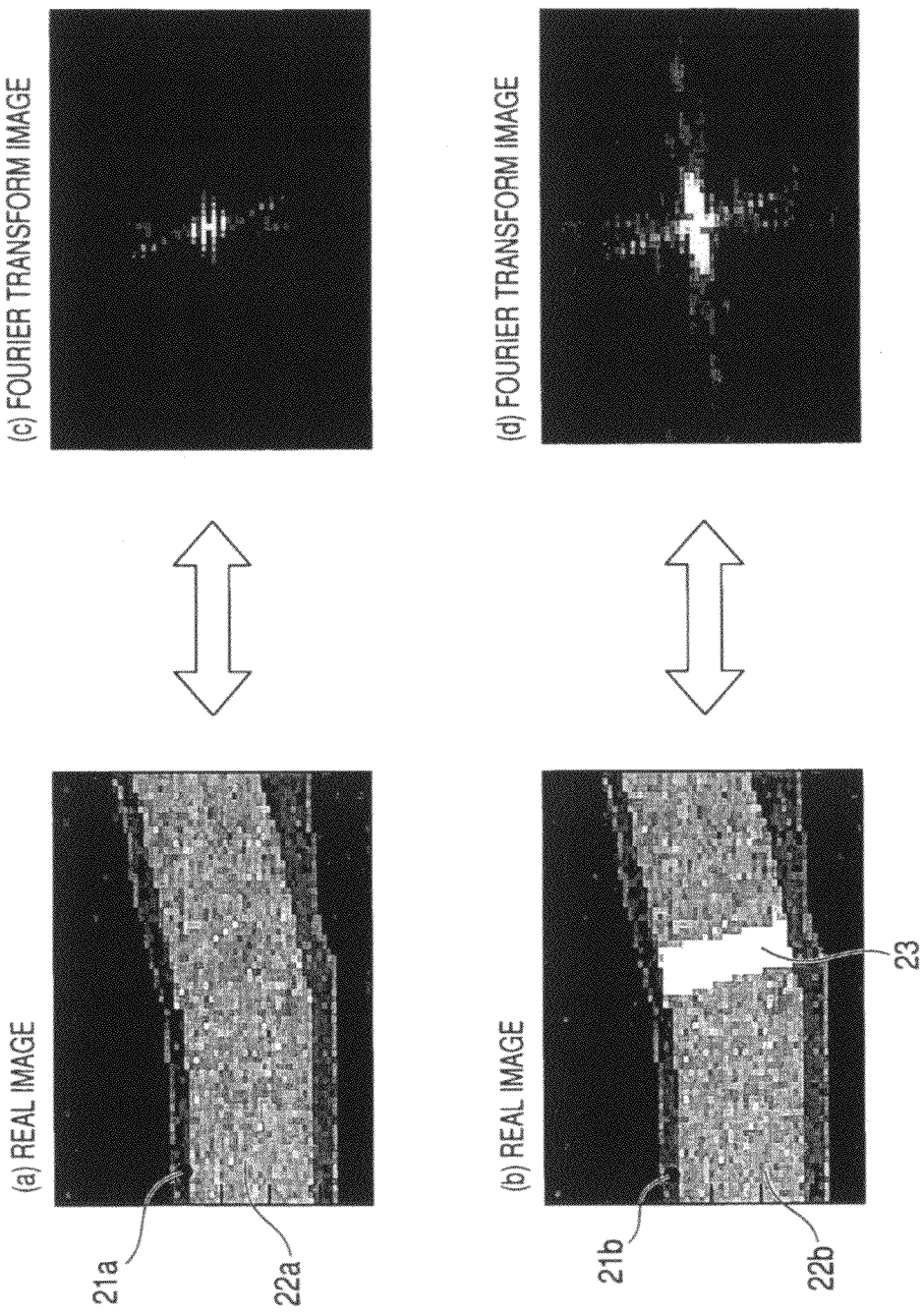
FIG. 2 is a schematic illustration of the real image and the Fourier transform image observed in Example 1.

Assume, for example, that the object of examination 13 is a person and a terahertz wave is irradiated onto one of the person's arms. In FIG. 2 (a) illustrates a schematic illustration of a real image that can be obtained when the person's arm with a long sleeve is observed by means of a terahertz wave. This corresponds to an arrangement where the detector 15 is arranged at the image plane 14b in FIG. 1. The arm 22a is visible through the translucent image of clothes 21a. In FIG. 2, (b) illustrates a schematic illustration of another real image that can be obtained when the person's arm with a long sleeve is observed by means of a terahertz wave. FIG. 2 illustrates a clasp cutter knife made of a non-metal material that is held by a wound rubber band 23 and hidden under the sleeve. In FIG. 2, the rubber band 23 wound around the arm 22b is shown white (the clasp cutter knife is not shown for the purpose of simplicity).

In FIG. 2, (c) illustrates a schematic illustration of a Fourier transform image obtained by observing the person's arm (carrying neither a knife nor a rubber band) by way of the terahertz optical system of FIG. 1 (the detector 15 being arranged at 14a). In FIG. 2, (d) illustrates a schematic illustration on another Fourier transform image obtained by observing the person's arm (carrying a knife and a rubber band) by way of the terahertz optical system of FIG. 1 (the detector 15 being arranged at 14a). Human skin and a rubber band show different reflection factors relative to a terahertz wave. Assume here that the rubber band shows a reflection factor higher than the human skin. DC components (components uniform over the entire image) appear at the center of an optically obtained Fourier transform image, whereas high frequency components of spatial frequencies appear in the peripheral area of the image. The image of (d) is extended more than the image of (c) in FIG. 2. This is attributable to the fact that the rubber band is smaller than the arm (and hence shows higher spatial frequencies). The image at and near the center is a Fourier transform image of the arm, whereas the extended image is a Fourier transform image of the rubber band.

The obtained Fourier transform image is then processed in the "spatial frequency filtering step" illustrated in the block diagram of FIG. 1. The filter that is employed in the spatial frequency filtering step needs to be selected appropriately according to the object of examination and the purpose of examination. In this Example, filtering is executed as described below by means of a visible light camera 17 adapted to pick up a visible light image (an image to be obtained by means of visible light) of the object of examination 13. A commercially available digital camera may be used as the visible light camera 17.

In FIG. 3, (a) illustrates a schematic illustration of the image of the person's arm, that is the object of examination, obtained by picking up a visible light image thereof by means of the visible light camera 17 and binarizing the picked up image. Since it is a visible light image, it does not show the inside of the clothes. The background is shown in black, whereas the clothes are shown in white. In FIG. 3, (b) illustrates a schematic illustration of the image obtained by subjecting the image of (a) in FIG. 3 to a Fourier transform processing, using a computer. The series of operations of binarization and Fourier transform correspond to the spatial frequency filter acquisition step illustrated in FIG. 1. The image of (b) in FIG. 3 is employed as spatial frequency filter and the difference between the image of (c) and that of (d) in FIG. 2, which are terahertz Fourier transform images, is determined.

In FIG. 4, (a) is a schematic illustration of an image obtained by way of a subtraction processing of subtracting the image of (b) in FIG. 3 (a Fourier transform image of a visible light image) from the image of (c) in FIG. 2 (a terahertz Fourier transform image of an arm not having any knife). In FIG. 4, (b) is a schematic illustration of an image obtained by way of a subtraction processing of subtracting the image of (b) in FIG. 3 (a Fourier transform image of a visible light image) from the image of (d) in FIG. 2 (a terahertz Fourier transform image of an arm having a knife). While only a slight image is left at and near the center of the image of (a) (of an arm having neither a knife nor a rubber band) in FIG. 4, a transversally oblong image is left in the image of (b) (of an arm having a knife and a rubber band) in FIG. 4.

The image obtained as a result of a spatial frequency filtering processing ((a) or (b) in FIG. 4) is displayed on the display section in FIG. 1. A commercially available liquid crystal display may be used for the display section. The examiner determines if something is hidden in the inside of the object of examination 13 (the inside of the clothes) or not from the image obtained as a result of the spatial frequency filtering processing and displayed on the display section. Nothing appears in the displayed image as (a) in FIG. 4 if nothing is hidden in the inside of the clothes, whereas something appears in the displayed image as (b) in FIG. 4 if an item smaller than the arm is hidden in the inside of the clothes. Any of the physical traits of the person can hardly be grasped from the images of (a) and (b) in FIG. 4 that are represented in a spatial frequency domain so that no invasion of privacy takes place but the object hidden in the inside of the clothes can be accurately detected.

To support the examiner's conjecture and determination, data on Fourier transform images of items to be identified that can be obtained by means of terahertz waves are preferably collected to form a database so that items may be identified by way of template matching processing, using the database.

With such an arrangement, the profile of an item hidden in the inside of the object of examination and/or a substance contained in the item can be identified highly accurately. Identification of new items may be possible if the database is updated.

An image such as (a) or (b) in FIG. 4 obtained by way of a spatial frequency filtering processing may be subjected to an inverse Fourier transform processing by means of a computer. This processing corresponds to the "inverse Fourier transform arithmetic operation step" in the block diagram of FIG. 1. In FIG. 4, (c) and (d) respectively illustrates the inverse Fourier transform images of (a) and (b). While (c) that is an inverse Fourier transform image of an arm carrying neither a knife nor a rubber band shows almost nothing, (d) that is an inverse Fourier transform image of an arm carrying a knife and a rubber band shows a real image 41 of the rubber band. That (d) in FIG. 4 does not show anything about the arm of the object of examination 13 should be noted here. This is because the image of the arm of the object of examination 13 is removed by the filtering processing executed by means of the visible light image. As a result, the examiner cannot grasp any of the physical traits of the object of examination 13 by seeing (d) in FIG. 4 and hence cannot invade the privacy of the object of examination 13. On the other hand, the examiner can accurately determine if the object of examination carries an object in the inside of the clothes.

Here again, a step of supporting the examiner's conjecture and determination may be executed by way of template matching processing of using a computer and a database. With such an arrangement, the profile of an item hidden in the inside of the object of examination and/or a substance contained in the item can be identified highly accurately.

The object of examination is assumed to be a person in this Example. The body and the apparel of a person are not particularly different from each other in terms of size. On the other hand, when a person hides an object in the inside of his or her clothes, the hidden object is naturally smaller than the body and the apparel of the person in size. The use of an image obtained by executing a Fourier transform processing on a visible light image as spatial frequency filer has an advantage of negating the person's body.

While a visible light image is employed as spatial frequency filter in this Example, some other technique may alternatively be used for the purpose of the present invention. For example, the average physique of persons may be stored in a database on the basis of the sexes, the races and the ages of objects of examination 13 and a Fourier transform image of the average physique of persons may be employed as filter.

While one or more than one Gunn diodes are employed as light source in this Example, the light source is not limited to one or more than one Gunn diodes so long as a coherent light source is provided. For example, a BWO (backward wave oscillator), a QCL (quantum cascade laser) or a terahertz parametric oscillator may alternatively be employed. Similarly, the detector may not necessarily be formed by a Schottky diode array and may alternatively be formed by a microbolometer array. While an array detector is preferably employed as detector for the purpose of reducing the examination time, a point detector may be operated to scan on a terahertz Fourier transform image. The detector may be arranged so as to operate also for spatial frequency filtering on a Fourier transform image.

While only one of the arms of an object of examination 13 is examined in this Example, the entire body of the object of examination 13 can be examined by sequentially examining all the other parts of the object of examination 13 including the trunk and the legs. The diameter of the collimated terahertz wave is 30 cm in the above description.

However, a terahertz wave can be collimated so as to show a diameter of about 2 m and a terahertz Fourier transform image of the entire body of an object of examination 13 can be obtained when the generated terahertz wave has a sufficient intensity and an optical system including large diameter lenses or mirrors is employed.

EXAMPLE 2

Spatial Frequency Filtering Using a Fourier Transform Image of the Second Electromagnetic Wave Now, the method of examining if an object of examination possesses a particular substance such as a narcotic or an explosive or not of Example 2 will be described below. As well known, narcotics and explosives have a characteristic absorption spectrum in the terahertz wave band, which is referred to as fingerprint spectrum. While the prior art fluoroscopy that employs scattered X-rays can detect if an object of examination possesses a nonmetal item or not, the prior art fluoroscopy cannot tell if the detected item is simply a plastic item or a plastic explosive. On the other hand, the method of examining by using a terahertz wave if an object of examination possesses a particular substance of this Example can tell if the detected item is simply a plastic item or a plastic explosive by analyzing the fingerprint spectrum of the substance of the item.

Figure 5:
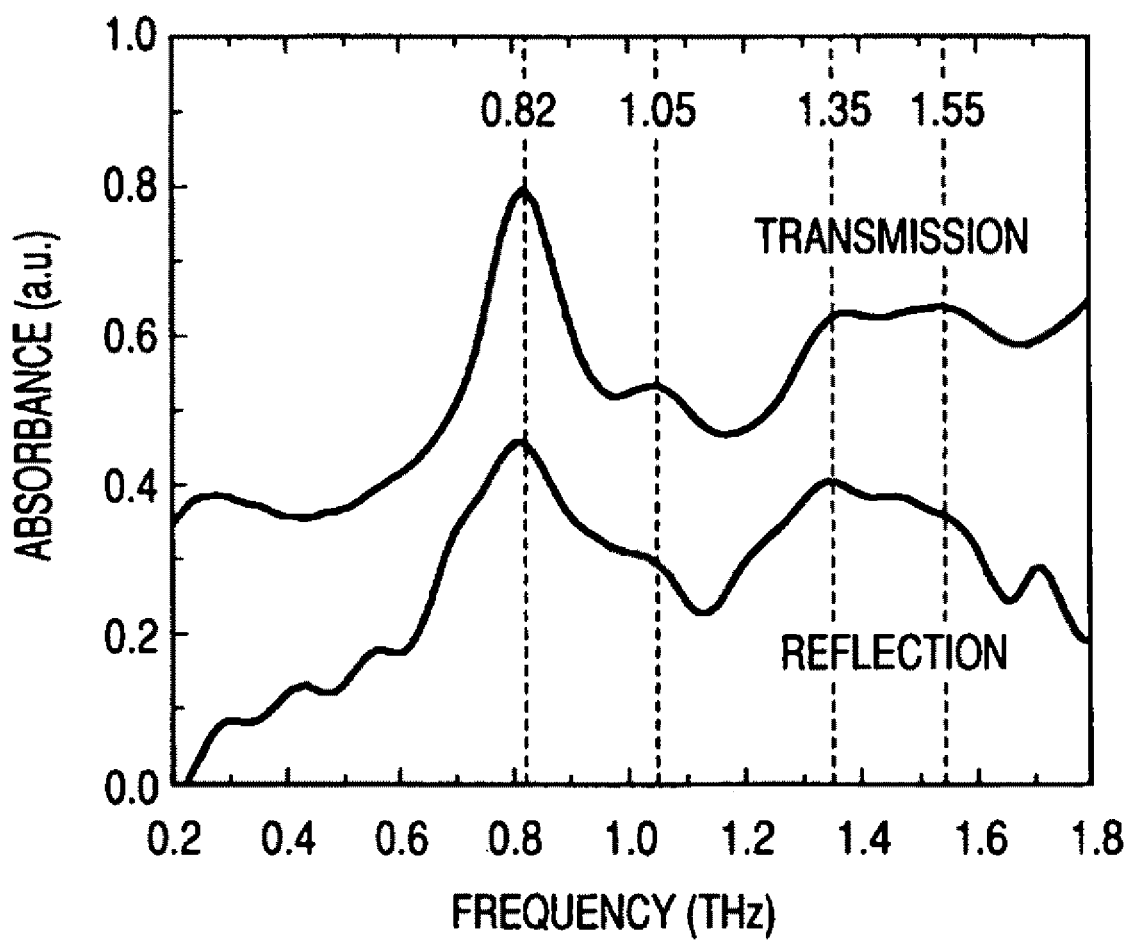
FIG. 5 is the absorption and reflection spectrums of the main ingredient RDX of a plastic explosive examined in Example 2 as object of examination.

For example, RDS (research department explosive; hexahydro-1,3,5-trinitro-1,3,5-triazine; also referred to as tri-methylene trinitromaine) has an absorption spectrum at and near 0.8 THz as illustrated in FIG. 5.

Note that FIG. 5 is cited from FIG. 3(c) of Hai-Bo Liu et al., OPTICS EXPRESS Vol. 14, p. 415 (2006). The title of the above document is "Detection and identification of explosive RDX by THz diffuse reflection spectroscopy".

If 0.8 THz at the peak of the absorption spectrum is compared with 1.0 THz at the outskirt of the absorption spectrum, 0.8 THz shows an absorption rate and a reflectivity that are about twice as high as 1.0 THz.

Figure 6:
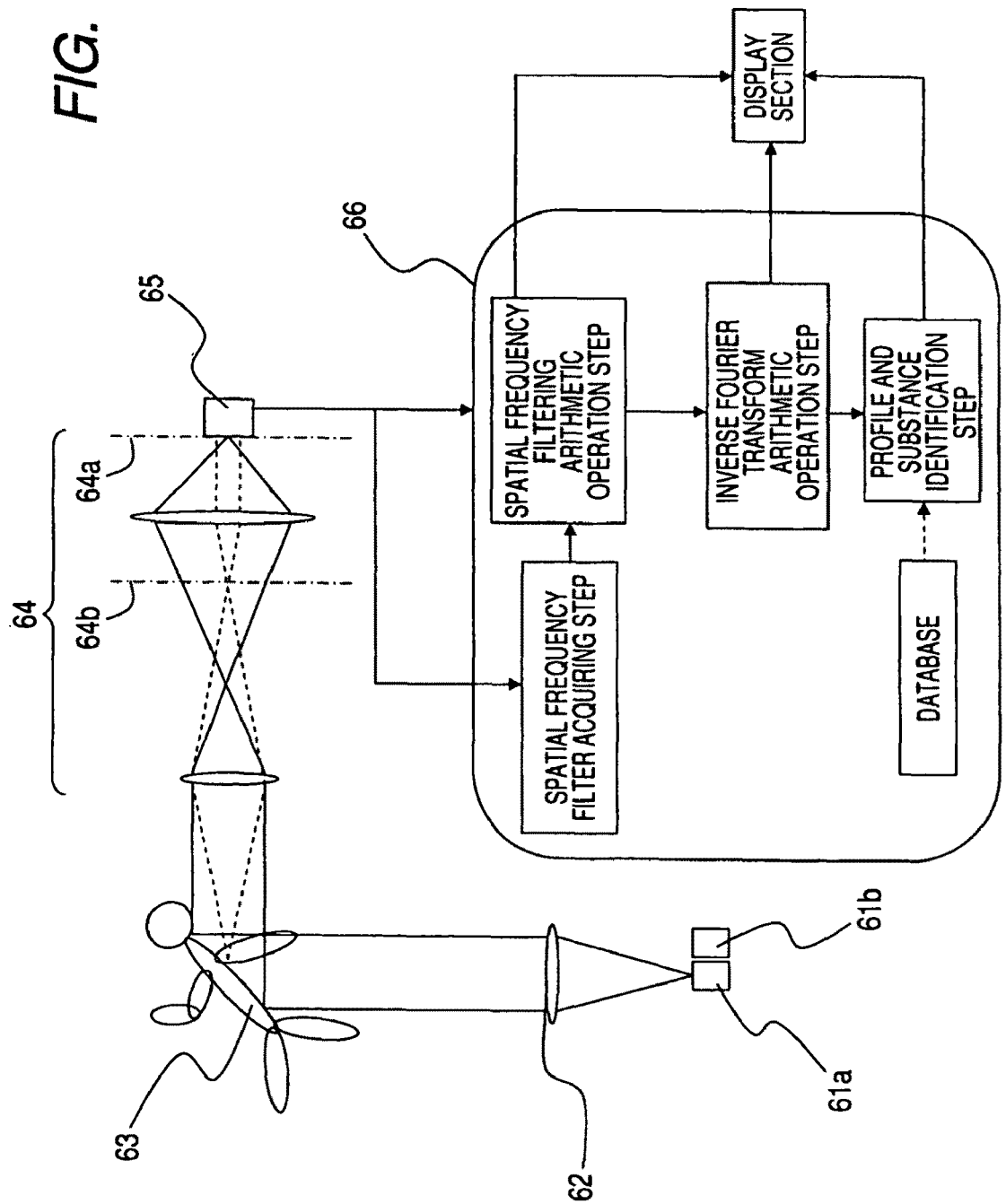
FIG. 6 is a schematic illustration of the imaging method and the imaging apparatus of Example 2.

In view of this fact, a device that causes two light sources 61a and 61b to generate terahertz waves having different center frequencies as illustrated in FIG. 6 is employed. Such a device may typically be formed by arranging two QCLs having different oscillation wavelengths side by side. Alternatively, such a device may be formed by using a terahertz-wave parametric oscillator that is a wavelength-tunable light source. Still alternatively, such a device may be formed by using a terahertz band gas laser whose oscillation wavelength can be selectively switched.

Figure 8:
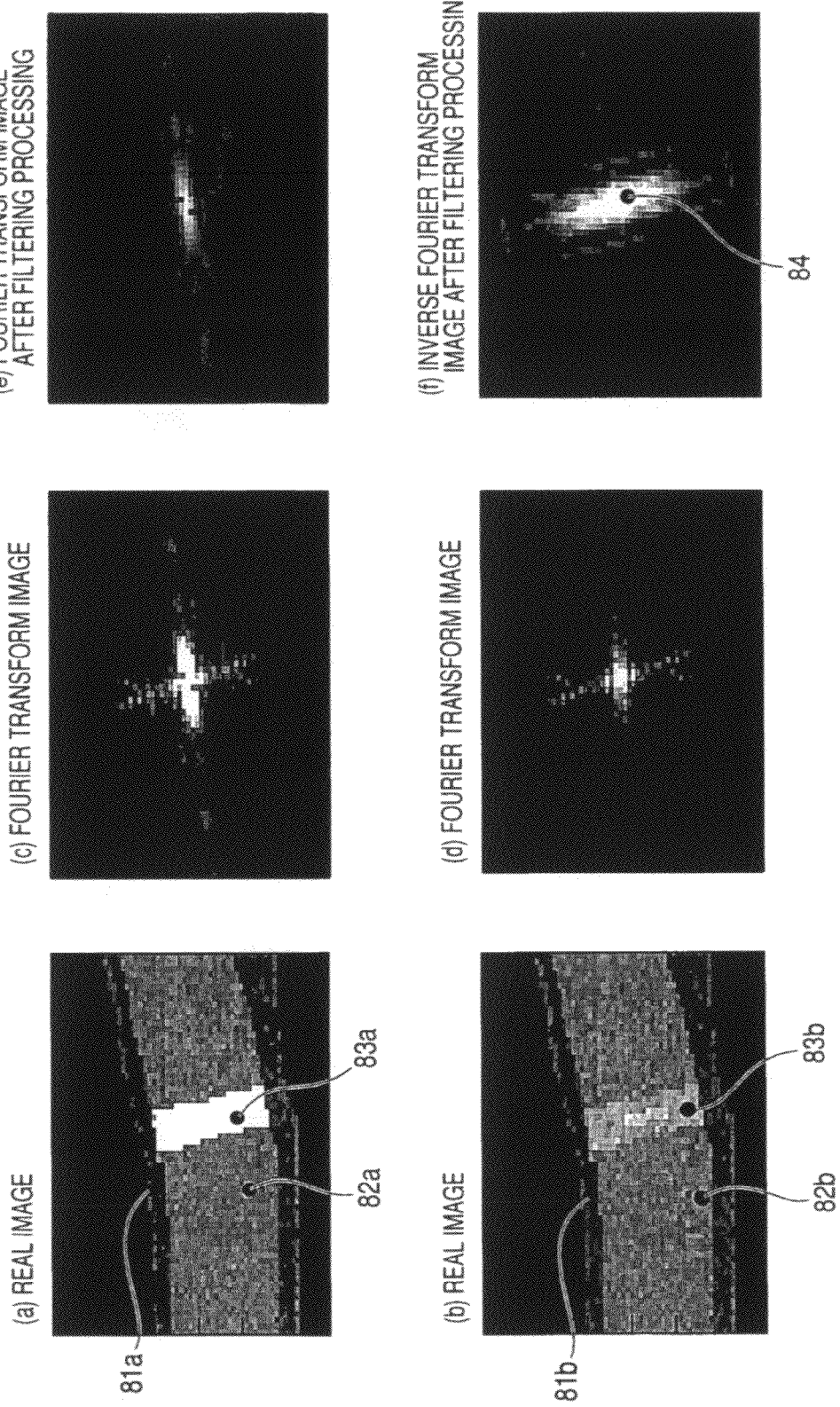
FIG. 8 is a schematic illustration of the real image, the Fourier transform image and the image obtained after executing the filtering processing observed in Example 2.

Firstly, a terahertz wave of the wavelength of 0.8 THz (the first electromagnetic wave or the first terahertz wave) is irradiated from the terahertz wave light source 61a of 0.8 THz onto the object of examination 63 that may be hiding RDX that needs to be detected if really hidden to obtain a terahertz wave Fourier transform image. Assume here that the object of examination 63 wears a long-sleeved garment as in the case of Example 1 and an explosive containing RDX as main ingredient is wound around one of the arms of the object of examination 63. A terahertz wave is collimated and irradiated onto the arm of the object of examination 63 by means of a terahertz wave irradiation optical system 62 and a Fourier transform image can be obtained by means of a Fourier transform optical system 64 and a terahertz wave detector 65 as in the case of Example 1. In FIG. 8, (a) is a schematic illustration of a real image that can be obtained when a terahertz wave of 0.8 THz is employed and the detector 65 is arranged at the position of 64b in FIG. 6. A plastic explosive 83a appears white there. In FIG. 8, (c) is a schematic illustration of the Fourier transform image obtained by arranging the detector 65 at the Fourier transform plane at 64a in FIG. 6.

Then, the light source is switched to the light source 61b and a Fourier transform image is obtained by means of a terahertz wave of the wavelength of 1.0 THz (the second electromagnetic wave or the second terahertz wave) in a similar manner. In FIG. 8, (b) is a schematic illustration of a real image that can be obtained when a terahertz wave of 1.0 THz is employed and the detector 65 is arranged at the position of 64b in FIG. 6. A plastic explosive 83b appears white there but less clear than the plastic explosive 83a. In FIG. 8, (d) is a schematic illustration of the Fourier transform image obtained by arranging the detector 65 at the Fourier transform plane at 64a in FIG. 6.

Now, the Fourier transform optical system 64 will be described below. If the size of the detector 65 is 10 mm as measured from the center to the periphery thereof and the wavelength is 0.3 mm, the lens focal length for Fourier transforms that allows the detector to detect up to a spatial frequency of 2 mm$^{-1}$ (a spatial resolution of 0.5 mm) is 16.7 mm and the lens focal length for Fourier transforms that allows the detector to detect up to a spatial frequency of 0.2 mm$^{-1}$ (a spatial resolution of 5 mm) is 167 mm. Therefore, a Fourier transform optical system that is formed by a group of a plurality of lenses including a relay lens having a long focal length and whose front focus is defined to be longer than the back focus can be used.

When the focal length is fixed, the size of Fourier transform image differs between 0.8 THz and 1.0 THz. For instance, the lens focal length that allows the detector to detect up to a spatial frequency of 0.2 mm$^{-1}$ (a spatial resolution of 5 mm) is 167 mm for 1.0 THz, whereas it is 133 mm for 0.8 THz. Therefore, a Fourier transform optical system 64 that is provided with a mechanism for making the focal length variable and adapted to produce Fourier transform images of the same size both for 0.8 THz and 1.0 THz is employed. For instance, such a variable focal length Fourier transform optical system can be formed by combining a convex lens and a concave lens and making the distance between the two lenses adjustable.

Figure 7:
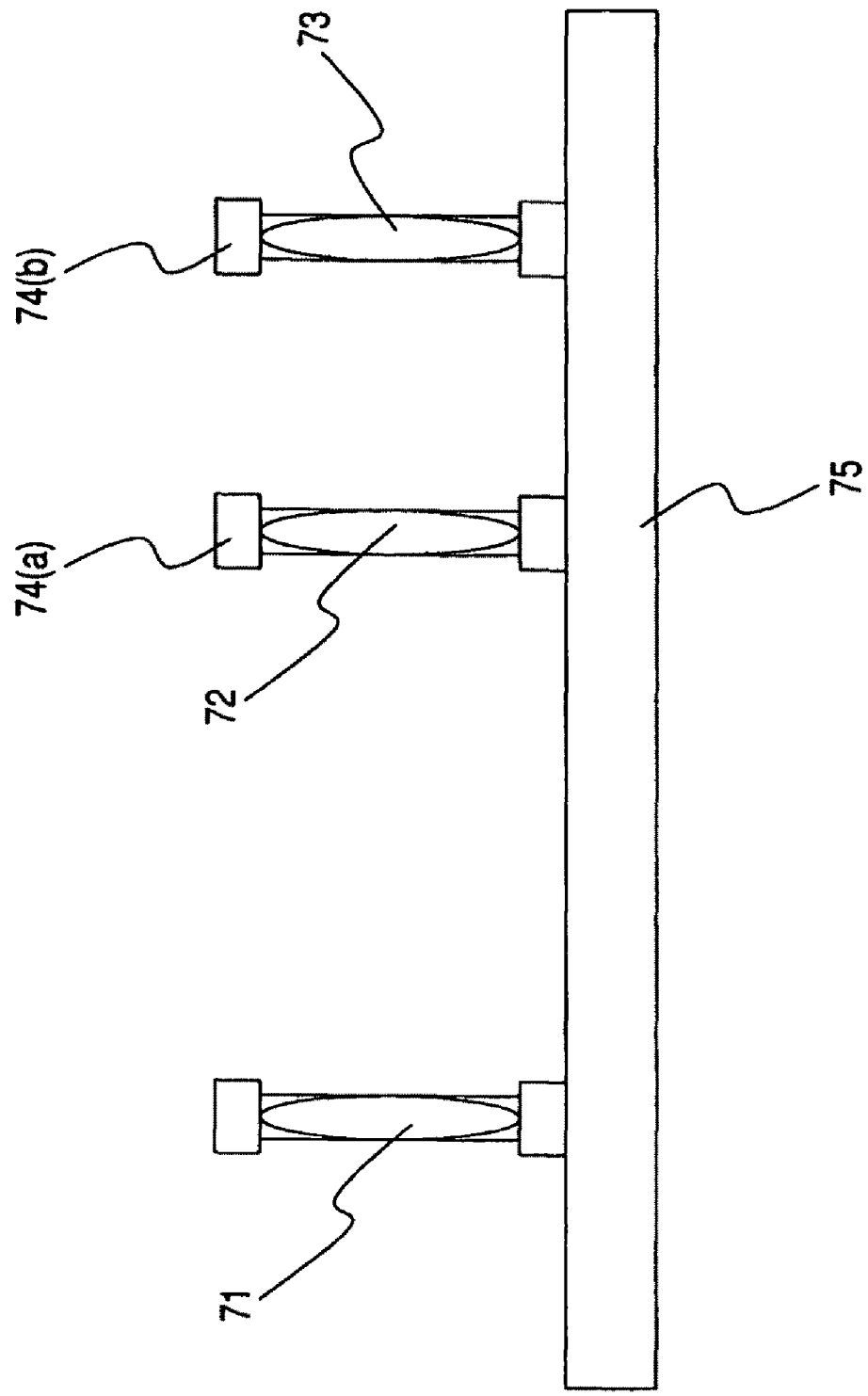
FIG. 7 is a schematic illustration of the variable focus Fourier transform optical system used in Example 2.

For example, a convex lens having a focal length of 50 cm is arranged at a position separated from the object of examination by 100 cm and operated as relay lens 71 as illustrated in FIG. 7. Another convex lens 72 having a focal length of 60 mm is arranged at a position separate from the relay lens 71 by 100 cm and a concave lens 73 having a focal length of 50 mm is arranged at a position separated from the convex lens 72 by 28 mm. As the convex lens 72 and the concave lens 73 are combined, they operate as a Fourier transform lens having a focal length of 166.7 mm. With this combination and arrangement, a Fourier transform image is obtained by using a terahertz wave having a frequency of 1 THz.

Then, the distance between the convex lens 72 and the concave lens 73 is shifted to 32.5 mm. As the inter-lens distance is altered, the combination operates as a Fourier transform lens having a focal length of 133.3 mm. With this combination and arrangement, a Fourier transform image is obtained by using a terahertz wave having a frequency of 0.8 THz. Thus, the size of the Fourier transform image on the detector can be held constant by altering the focal length if the frequency of terahertz wave is switched.

In this Example, a mechanism for mechanically shifting the positions of two lenses is adopted as mechanism for altering the focal length of the Fourier transform lens as illustrated in FIG. 7. For shifting the distance between two lenses, the lenses are held by respective lens holders 74a and 74b, which are held on an optical rail 75 and driven to slide. Note that, the ratios of distances do not necessarily reflect the real values in FIG. 7 so that the characteristics of the components may be recognized clearly.

The arrangement preferably includes a mechanism for altering the relative distance between the Fourier transform optical system 64 and the object of examination 63 both in the direction of the optical axis and in a direction perpendicular to the optical axis. For instance, the Fourier transform optical system may be arranged on a tripod equipped with casters. In a preferable mode of realizing the present invention, both a variable focus mechanism and a mechanism for altering the relative distance between the Fourier transform optical system 64 and the object of examination 63 in the direction of the optical axis and in a direction perpendicular to the optical axis are provided.

In this Example, the Fourier transform image obtained by means of a terahertz wave of 1.0 THz is operated as spatial frequency filter. In other words, the Fourier transform image obtained by means of a terahertz wave of 1.0 THz is sent to the spatial frequency filter acquisition step of FIG. 6.

The Fourier transform image obtained by a terahertz wave of 0.8 THz and the Fourier transform image obtained by a terahertz wave of 1.0 THz in the spatial frequency filter arithmetic operation step in FIG. 6 are subjected to a subtraction processing. In FIG. 8, (e) is a schematic illustration of the result of the subtraction processing. In FIG. 8, (f) is a schematic illustration of the outcome of the inverse transform executed on (e) of FIG. 8 in the inverse Fourier transform arithmetic operation processing. A plastic explosive 84 clearly appears there. The image of (e) or (f) of FIG. 8 is displayed on the display section to the examiner. It may be checked by referring to the information of a database to support the examiner determining if the object of examination 63 has RDX or not.

The reflectivity of skin and that of clothing relative to a terahertz wave do not differ from each other significantly between 0.8 THz and 1.0 THz that are relatively close to each other. When the substance that the object of examination 63 has is simply a plastic substance, the obtained two Fourier transform images are substantially same because the reflectivity does not differ significantly between 0.8 THz and 1.0 THz. Thus, a black image where all the values are substantially equal to nil is obtained as a result of a subtraction processing because the two Fourier transform images negate each other. On the other hand, when the object of examination 63 has a substance such as RDX whose reflectivity varies significantly between 0.8 THz and 1.0 THz, only the item having such a variable reflectivity is obtained as a real image as illustrated in (d) of FIG. 8.

A substance can be identified more accurately by using terahertz waves of many different frequencies. The level of accuracy can be raised by using terahertz waves of three or four different frequencies (the third electromagnetic wave, the fourth electromagnetic wave).

There may accidentally be a substance other than RDX that has an absorption peak at or near 0.8 THz. However, when similar step are executed by using close frequencies such as 1.35 THz and 1.5 THz and a visible light image is obtained with both of the frequencies, the object of examination highly possibly has RDX. When, on the other hand, a visible light image is obtained only with the 0.8 THz, the object of examination highly possibly has a substance other than RDX having an absorption peak at 0.8 THz. Such identification of a substance is conducted in the "profile/substance identification step" that a computer 66 executes.

This Example again does not visualize a real image of the inside of the clothes of the object of examination but extracts and visualizes only the substance to be detected so that no invasion of privacy takes place. Additionally, this Example only extracts and visualizes a particular substance such as plastic explosive on the basis of the fingerprint spectrum thereof to ensure a highly reliable effect of examination.

EXAMPLE 3

Transmission Type

Figure 9:
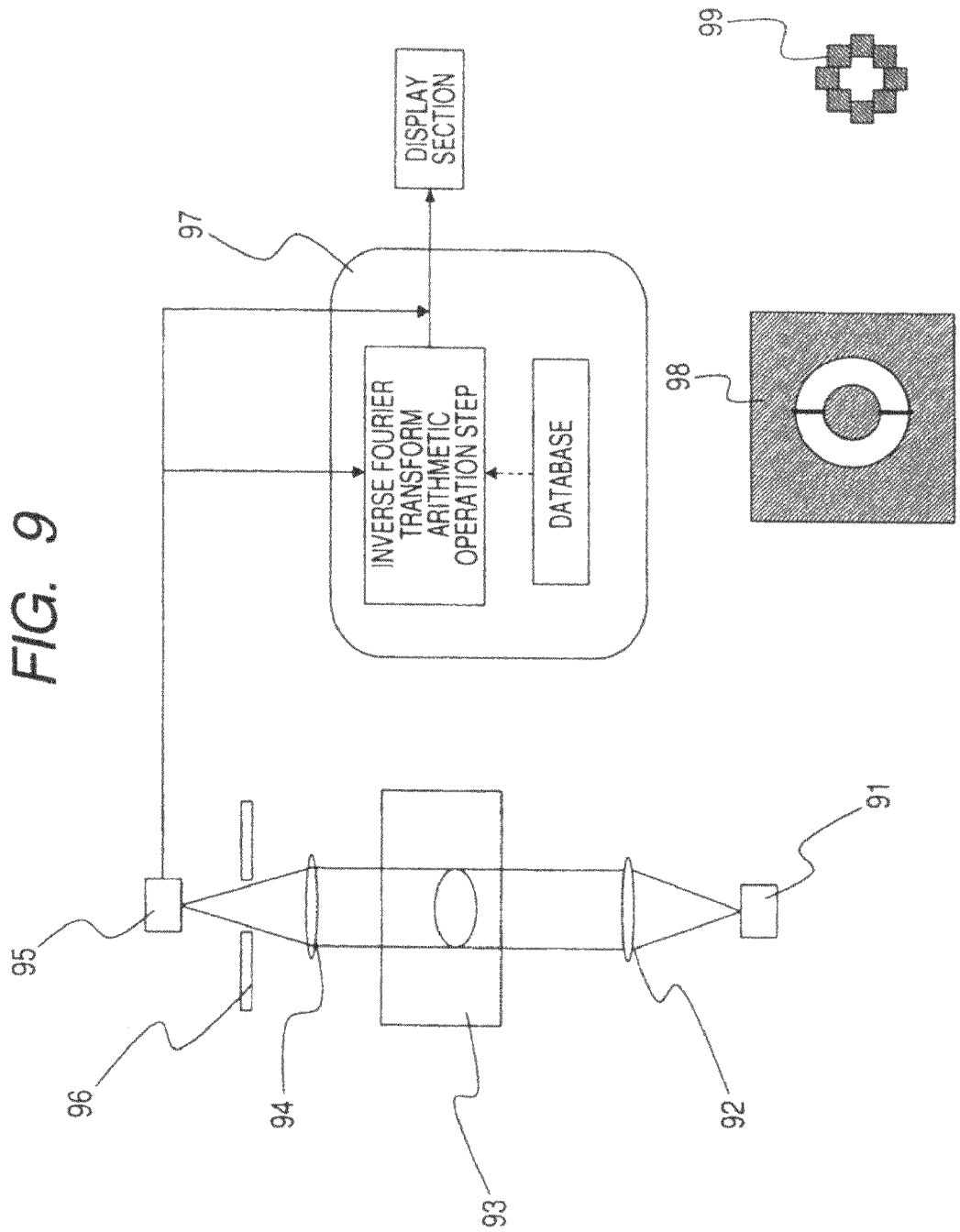
FIG. 9 is a schematic illustration of the imaging method and the imaging apparatus of Example 3 that employed an optical filter.

Now, Example 3 will be described below by referring to FIG. 9.

Assume here that the object of examination 93 is a sealed letter that may contain a narcotic or an explosive. The terahertz wave emitted from a terahertz wave light source 91 (e.g., a gas laser of 3.0 THz) is collimated by an irradiation optical system 92 to parallel rays of light. The collimated terahertz wave is then irradiated onto an object of examination 93. The terahertz wave that is scattered and transmitted is transmitted through a Fourier transform optical system 94 and then forms a Fourier transform image of the object of examination 93 at a detector 95.

The terahertz wave that is scattered by the character part in the sealed letter that is written by means of a pencil, toner or ink is diffracted to a peripheral part of the Fourier transform image obtained as a high spatial frequency component. On the other hand, the narcotic or the explosive contained in the sealed letter has a size probably larger than the characters written there but smaller than the entire sealed letter. Then, the narcotic or the explosive appears at a position moderately remote from the center of the Fourier transform image as a spatial frequency component of a medium degree. A diffracted image of the entire sealed letter appears at the center of the Fourier transform image. Thus, the high spatial frequency component and the low spatial frequency component are optically removed by means of a spatial frequency filter 96. A ring-shaped metal plate 98 may be used for the spatial frequency filter 96. This is a so-called band pass filter. Alternatively, the detector 95 may be formed as a single device detector and a ring-shaped detector array 99 formed by arranging detectors only at parts where the intermediate spatial frequency component is diffracted may be employed. This is a mode of carrying out the invention where a spatial frequency filter and a detector are integrated.

The terahertz Fourier transform image that is optically subjected to a spatial frequency filtering processing and detected by the detector 95 is then displayed on the display section to the examiner by way of a computer 97. Alternatively, the terahertz Fourier transform image may be subjected to an inverse Fourier transform by means of a computer (inverse Fourier transform arithmetic operation processing) and subsequently displayed on the display section to the examiner.

Figure 10:
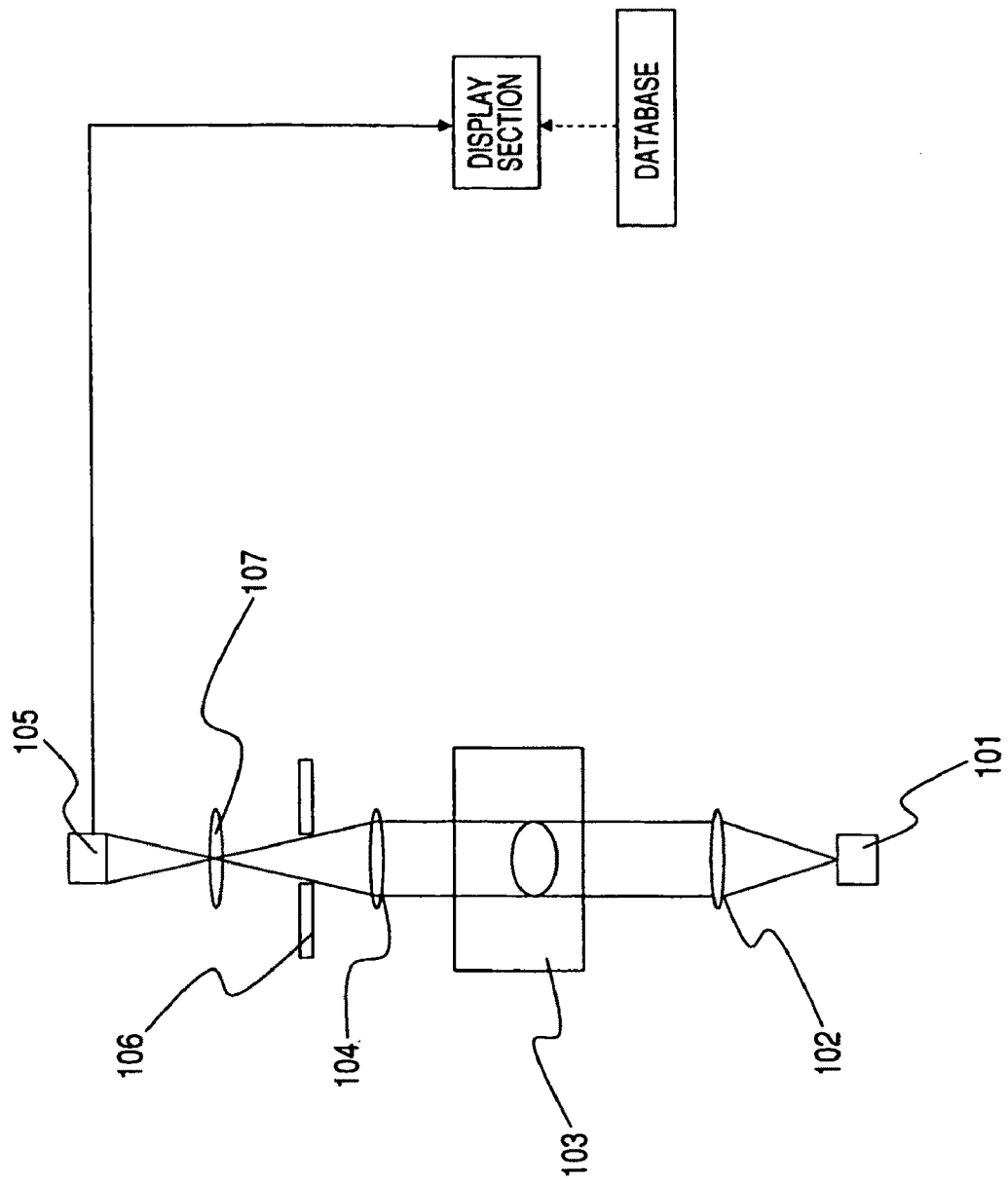
FIG. 10 is a schematic illustration of the optical inverse Fourier transform optical system used in Example 3.

Still alternatively, the inverse Fourier transform arithmetic operation processing may be executed not by means of a computer but optically. In other words, an inverse Fourier transform optical system 107 as illustrated in FIG. 10 may be used.

EXAMPLE 4

Generation of a Continuous Wave Having a Difference Frequency

Figure 11:
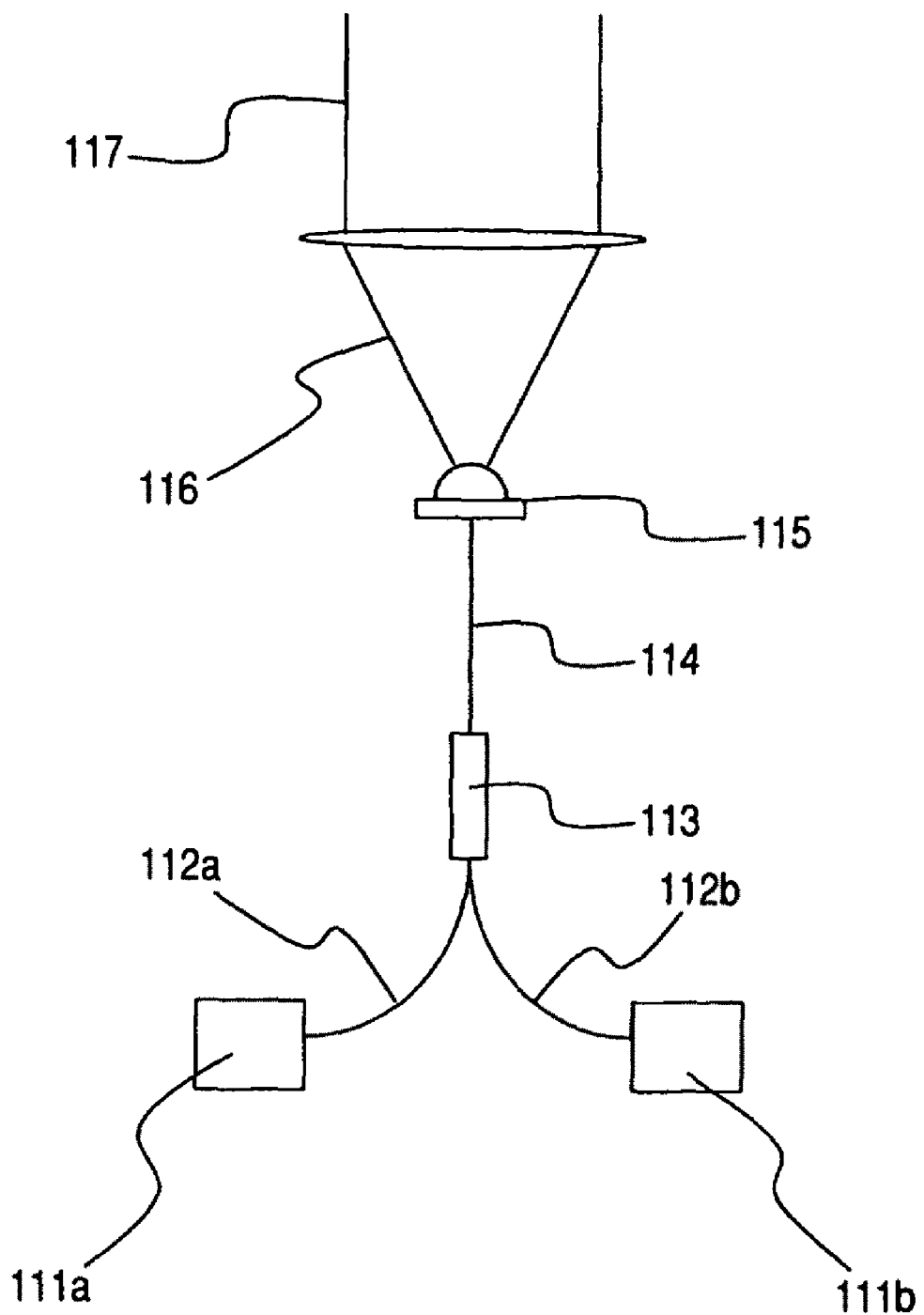
FIG. 11 is a schematic illustration of the imaging method and the imaging apparatus of Example 4 that employed a differential frequency generation method.

Now, Example 4 will be described below by referring to FIG. 11.

The laser beams emitted from semiconductor lasers 111*a* and 111*b* are put together by a coupler 113 after passing through optical fibers 112*a* and 112*b* respectively. The coupled laser beam is made to pass through an optical fiber 114 and enter a photoconductive device 115. The photoconductive device 115 is a device having a pair of electrodes on a compound semiconductor such as low temperature grown gallium arsenide, where the paired electrodes are arranged opposite to each other typically with a gap of 5 μm separating them from each other. As the laser beam is irradiated onto the gap with a voltage of about 10V relative to the paired electrodes, a terahertz wave having a frequency corresponding to the frequency difference of the two laser beams from the two semiconductor lasers 111*a* and 111*b* is generated. For instance, if the wavelength of the laser beam emitted from the laser 111*a* is 780 nm and that of the laser beam emitted from the laser 111*b* is 778 nm, a terahertz wave of a frequency of 1 THz is generated from the photoconductive device 115. This technique is referred to as difference-frequency generation method or beam method.

The terahertz wave generated by the difference-frequency generation method is characterized by being coherent continuous light. The frequency of the generated terahertz wave can be made variable by using an external cavity wavelength-tunable laser for one of the semiconductor lasers (e.g., the laser 111*a*).

The generated terahertz wave 116 is turned to collimated light 117 by means of a lens and irradiated onto an object of examination. After the irradiation on the object of examination, a Fourier transform image is obtained by way of a process similar to that of Example 1.

Since the frequency of the terahertz wave is continuously variable with the method of this example, the method can be effectively used for detecting various substances having different absorption spectrums.

EXAMPLE 5

Electro-Optical Sampling Method

Figure 12:
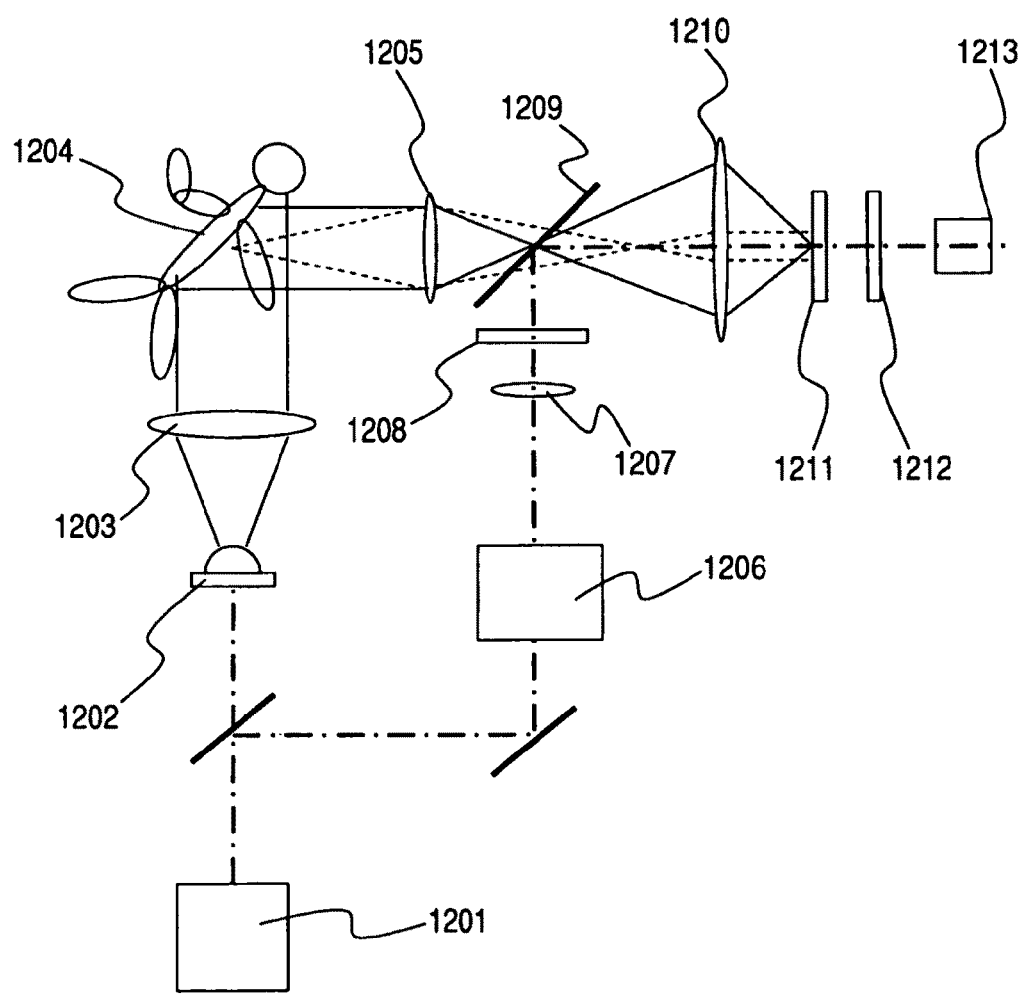
FIG. 12 is a schematic illustration of the imaging method and the imaging apparatus of Example 5 that employed an electro-optical sampling method.

Now, Example 5 will be described below by referring to FIG. 12.

The laser beam emitted from regenerative amplification mode-locked titanium-sapphire laser 1201 is bifurcated by a beam splitter and one of the laser beams enters photoconductive device 1202. The pulse-shaped terahertz wave generated from the photoconductive device is collimated by lens 1203 and subsequently irradiated onto an object of examination 1204. The terahertz wave is scattered by the object of examination 1204 and forms a Fourier transform image on about 2 mm-thick ZnTe crystal 1211 by way of lenses 1205 and 1210. The other laser beam produced from the beam splitter joins with the terahertz wave at a pellicle 1209 by way of a time-delay device 1206, a lens 1207 and a polarizer 1208. The laser beam transmitted through the lens 1210 and the ZnTe crystal 1211 is partly elliptically polarized by the electro-optical effect of the terahertz wave. The intensity of the laser beam reflects the intensity of the terahertz wave as they pass the analyzer 1212. A 2D image of the terahertz wave can be obtained by shooting the intensity of the laser beam by means of a CCD camera 1213. This method is a so-called electro-optical (EO) sampling method.

A Fourier transform image of the object of examination 1204 is optically acquired by means of the EO sampling method. The terahertz wave to be used for the EO sampling method is a pulse-shaped terahertz wave. Typically, it is a broadband terahertz wave including a frequency band from 0.3 to 3.0 THz. The temporal waveform of the terahertz wave can be obtained by using a time-delay device 1206 and the frequency spectrum can be obtained by subjecting the terahertz wave to frequency domain Fourier transform (not spatial Fourier transform). Thus, a Fourier transform image over a broad frequency domain can be obtained by means of the EO sampling method.

EXAMPLE 6

Figure 13:
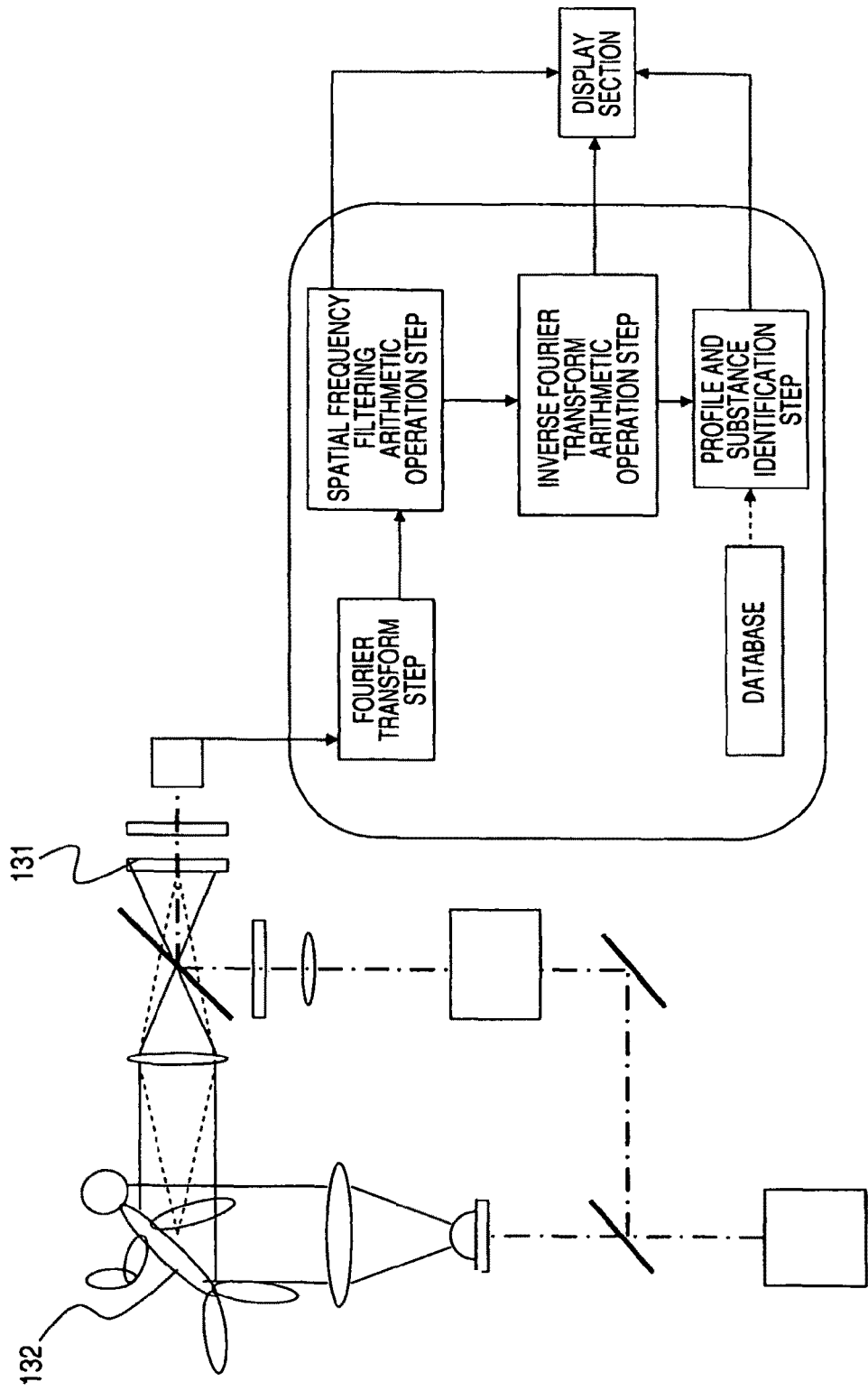
FIG. 13 is a schematic illustration of the imaging method and the imaging apparatus of Example 6 that electronically Fourier transformed the real image by an electro-optical sampling method.

A Real Image is Subjected to Spatial Fourier Transform by Way of an Electric Arithmetic Operation Processing Referring now to FIG. 13, a terahertz image of a real image of an object of examination 132 can be obtained by means of the EO sampling method by arranging a ZnTe crystal 131 at a position where a real image of the scattered terahertz wave from the object of examination 132 can be obtained. The terahertz image is not directly displayed on the display section but subjected to spatial Fourier transform by way of electronic arithmetic processing and subsequent spatial frequency filtering before the terahertz image can be displayed on the display section.

This method can use any of various filters (including a hamming filter and a hanning filter) in the course of electronic Fourier transform and hence is effective in terms of noise reduction.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-226339, filed Aug. 31, 2007, and No. 2008-160767 filed Jun. 19, 2008 which are hereby incorporated by reference herein in their entirety.

The invention claimed is:

1. An imaging method using an electromagnetic wave, comprising:
a first generation step of generating a first electromagnetic wave comprising a terahertz wave;
a step of acquiring a first Fourier transform image of an object of examination, using the first electromagnetic wave generated in the generation step and transmitted through or reflected by the object of examination;
a step of acquiring a second Fourier transform image to be used as a spatial frequency filter for the first Fourier transform image; and
a step of executing an arithmetic operation processing on the first Fourier transform image and the second Fourier transform image,
wherein the second Fourier transform image is a Fourier transform image of the object of examination acquired by using a second electromagnetic wave which has a center frequency different from a center frequency of the first electromagnetic wave, and
wherein the step of executing an arithmetic operation processing includes calculating a difference between the second Fourier transform image and the first Fourier transform image.

2. The method according to claim 1, wherein the method further comprises a step of collimating the generated first electromagnetic wave, and the first Fourier transform image is optically acquired.

3. The method according to claim 1, wherein the step of acquiring a first Fourier transform image includes:
a step of optically acquiring a real image of the object of examination, using the first electromagnetic wave generated in the generation step and transmitted through or reflected by the object of examination; and
a step of subjecting the real image to Fourier transform by way of an electric arithmetic operation processing.

4. The method according to claim 1, wherein the step of acquiring a second Fourier transform image includes:
a step of acquiring a real image of the object of examination by means of the second electromagnetic wave which comprises a visible light;
a step of acquiring a binarized image of the real image; and
a step of subjecting the binarized real image to Fourier transform by way of an electric arithmetic operation processing.

5. The method according to claim 1, wherein the step of acquiring a second Fourier transform image includes:
a second generation step of generating the second electromagnetic wave comprising a terahertz wave having a center frequency different from the terahertz wave generated in the first generation step; and
a step of optically acquiring a Fourier transform image of the second electromagnetic wave transmitted through or reflected by the object of examination.

6. The method according to claim 1, wherein the step of acquiring a second Fourier transform image includes:
a step of reading out a body profile corresponding to the object of examination from average body profiles of different sexes, different ages and different nationalities stored in advance; and
a step of executing Fourier transform on the body profile corresponding to the object of examination.

7. The method according to claim 1, wherein the second Fourier transform image is optically removed or subtracted by way of an electric arithmetic operation processing from the first Fourier transform image in the step of executing an arithmetic operation processing on the first Fourier transform image and the second Fourier transform image.

8. The method according to claim 1, wherein the method further comprises a step of acquiring an inverse Fourier transform image of the image acquired in the step of executing an arithmetic operation processing on the first Fourier transform image and the second Fourier transform image.

9. An imaging apparatus, comprising:
an irradiation unit for irradiating an object of examination with a collimated coherent electromagnetic wave;
an acquisition unit constructed to acquire a Fourier transform image of the object of examination, using the transmitted electromagnetic wave or the reflected electromagnetic wave from the object of examination by means of an optical unit; and
a spatial frequency filtering unit constructed to execute a spatial frequency filtering processing on the Fourier transform image,
wherein the acquisition unit is constructed to acquire a first Fourier transform image of the object of examination, using a first electromagnetic wave comprising a terahertz wave used for irradiating the object of examination and transmitted or reflected from the object of examination, and constructed to acquire a second Fourier transform image of the object of examination which is to be used as a spatial frequency filter for the first Fourier transform image, using a second electromagnetic wave used for irradiating the object of examination and transmitted or reflected from the object of examination, wherein the first electromagnetic wave and the second electromagnetic wave have center frequencies different from each other, and wherein the spatial frequency filtering unit is constructed to calculate a difference between the second Fourier transform image and the first Fourier transform image.

10. The apparatus according to claim 9, wherein the apparatus further comprises an inverse unit constructed to execute inverse Fourier transform on the Fourier transform image subjected to the spatial frequency filtering processing.

11. The apparatus according to claim 9, wherein an optical system formed by using a plurality of lenses or mirrors is employed for the acquisition unit, and wherein the distance from an optical plane closest to the object of examination out of optical planes of the optical system to the object of examination is greater than the distance from an optical plane closest to a detector out of the optical planes of the optical system to the detector.

12. The apparatus according to claim 9, wherein the acquisition unit has a lens or a mirror for forming a focused real image of the object of examination and a lens or a mirror for forming a Fourier transform image of the real image.

13. The apparatus according to claim 9, wherein an optical system is employed for the acquisition unit, and the optical system has a variable focus unit and a unit constructed to change the relative distance between the object of examination and the acquisition unit or both of them.

14. The apparatus according to claim 11, wherein the detector also operates for spatial frequency filtering on the Fourier transform image.

15. The method according to claim 1, wherein the second electromagnetic wave comprises visible light or a terahertz wave.

16. The apparatus according to claim 9, wherein the second electromagnetic wave comprises visible light or a terahertz wave.

* * * * *